US008658087B2

United States Patent
Lepez

(10) Patent No.: US 8,658,087 B2
(45) Date of Patent: Feb. 25, 2014

(54) METHOD OF TREATING SUBSTANCES IN DIVIDED SOLID FORM FOR THERMAL DEBACTERIZATION, AND AN INSTALLATION FOR IMPLEMENTING SAID METHOD

(75) Inventor: Olivier Lepez, Lamorlaye (FR)

(73) Assignee: E.T.I.A.—Evaluation Technologique, Ingenierie et Applications, Compiegne (FR)

( * ) Notice: Subject to any disclaimer, the term of this patent is extended or adjusted under 35 U.S.C. 154(b) by 775 days.

(21) Appl. No.: 12/708,925

(22) Filed: Feb. 19, 2010

(65) Prior Publication Data

US 2011/0171063 A1   Jul. 14, 2011

(30) Foreign Application Priority Data

Jan. 8, 2010   (FR) ...................................... 10 50089

(51) Int. Cl.
*A61L 2/07* (2006.01)
(52) U.S. Cl.
USPC .............................................. 422/26; 422/32
(58) Field of Classification Search
USPC .................................................... 422/26, 32
See application file for complete search history.

(56) References Cited

U.S. PATENT DOCUMENTS

| | | | |
|---|---|---|---|
| 3,137,630 A * | 6/1964 | Hecker et al. | 264/14 |
| 4,036,938 A * | 7/1977 | Reed | 423/483 |
| 6,375,345 B1 | 4/2002 | Lepez et al. | |
| 6,562,396 B1 | 5/2003 | Minier et al. | |
| 2003/0119909 A1* | 6/2003 | Stanislaus | 514/562 |

FOREIGN PATENT DOCUMENTS

| | | |
|---|---|---|
| FR | 2788336 A1 | 7/2000 |
| WO | 99/39549 A1 | 8/1999 |
| WO | 99/65332 A1 | 12/1999 |
| WO | 2009/133321 A2 | 11/2009 |

* cited by examiner

*Primary Examiner* — Lyle Alexander
(74) *Attorney, Agent, or Firm* — McCormick, Paulding & Huber LLP

(57) ABSTRACT

The invention relates to a method of treating substances in divided solid form for thermal debacterization, in which the substances are stirred in a closed enclosure provided internally with controlled heating contact wall means acting directly on the substances while they are being stirred. In accordance with the invention, the substances for treatment are previously mixed, prior to reaching an inlet to the closed enclosure, with an anti-clumping agent likewise in the form of divided solids, the mixture then being stirred in the closed enclosure while being subjected to the combined action of the heating contact walls and of the superheated wet steam, and being recovered at an outlet of the closed enclosure.

9 Claims, 1 Drawing Sheet

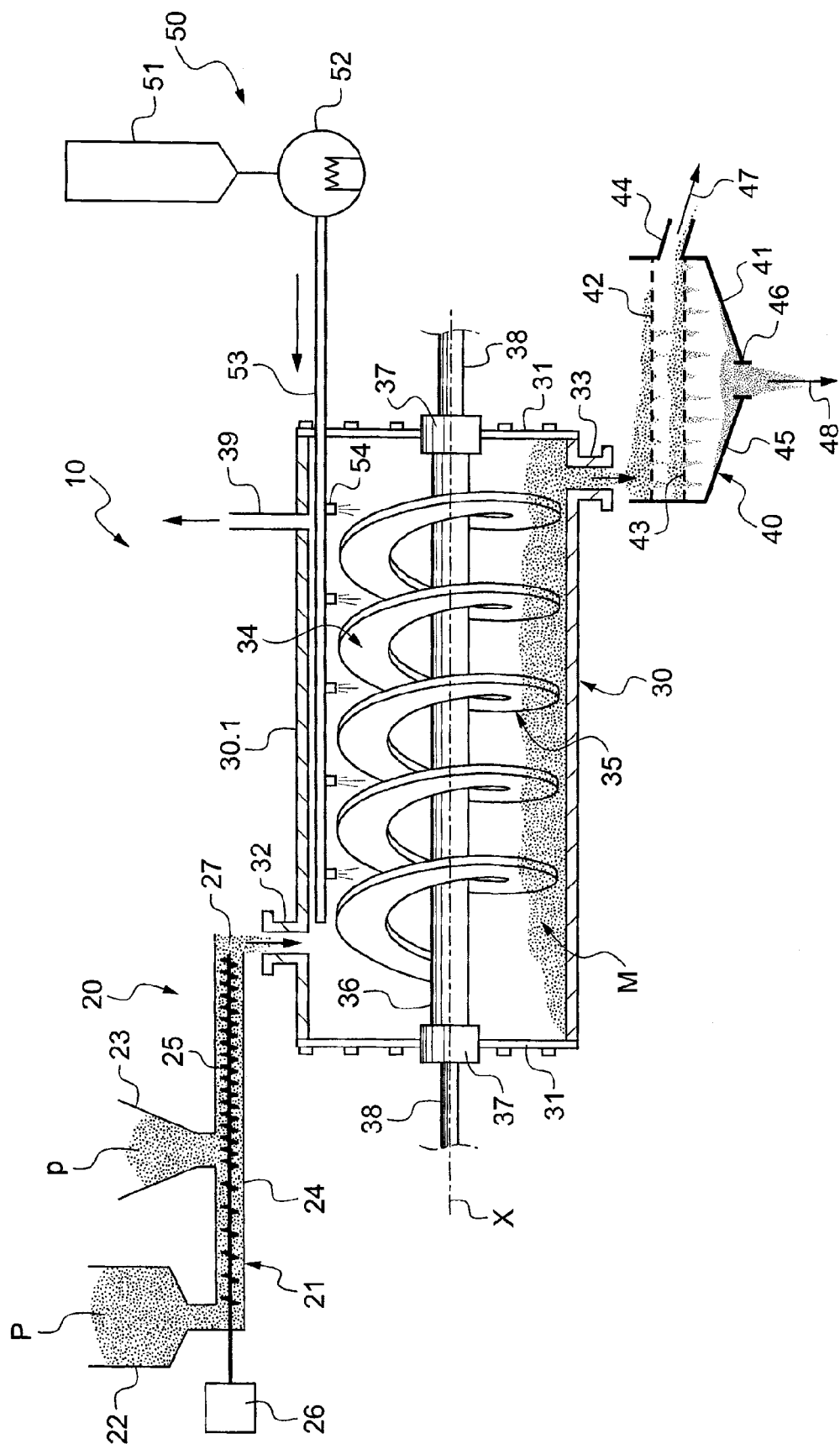

METHOD OF TREATING SUBSTANCES IN DIVIDED SOLID FORM FOR THERMAL DEBACTERIZATION, AND AN INSTALLATION FOR IMPLEMENTING SAID METHOD

CROSS REFERENCE TO RELATED APPLICATIONS

Applicant hereby claims foreign priority benefits under U.S.C. §119 from French Patent Application No. 10 50089 filed on Jan. 8, 2010, the contents of which are incorporated by reference herein.

FIELD OF THE INVENTION

The present invention relates to treating substances in divided solid form for thermal debacterization.

BACKGROUND OF THE INVENTION

Discontinuous debacterization methods are known that comprise a treatment enclosure fitted internally with heating contact walls and with means for injecting steam under pressure, such methods making use of installations of large dimensions with high production costs.

Continuous debacterization methods are also known that comprise a treatment enclosure having a double-walled conveyor screw located therein, with a heat-conveying fluid being caused to pass therethrough and with steam also being injected into the enclosure. Because the steam condenses, it is found that the substance becomes wet, thus requiring it to be subjected subsequently to drying treatment.

The same drawback is to be found with fluidized vibrating bed type conveyors or with pressurized gravity tube systems having the substances flowing therethrough. A high operating pressure, e.g. of the order of 10 bars, is sometimes even used, as described in document FR-A-2 788 336, thereby constituting a considerable constraint on implementing the method.

Electric current conveying vibrating tube type conveyors have also been used, as described in document WO-A-99/65332, however the heat exchange, which is mainly conductive, can lead to very large temperature gradients, thus giving rise to sticking as a result of the substance burning against the inside wall of the tube when the setpoint temperature lies above a degradation temperature for the substance.

Proposals have also been made for conveyor systems using a screw that conveys electrical current directly, as described in document WO-A-99/39549 in the name of the Applicant. In such systems, the substances are conveyed while simultaneously being stirred and heated by coming directly into contact with a conveyor screw that is itself heated by the Joule effect.

More recently, the above-mentioned system has been further improved by providing for wet steam at atmospheric pressure to be injected into the closed conveyor enclosure, which steam is previously superheated prior to penetrating into the enclosure by a member for heating gaseous fluid and that is located outside the enclosure. It is then possible to control the system in such a manner that the temperature of the superheated wet steam inside the closed enclosure at atmospheric pressure remains substantially equal to the temperature of the heating contact walls that act directly on the substances while they are being conveyed. For greater detail, reference may be made to document WO-A-2009/133321 in the name of the Applicant.

Those techniques give results that are entirely satisfactory with substances in divided solid form that present a mass with good fluidity. This applies for example when treating peppercorns or coriander seeds or hazel nuts. It then suffices to organize effective stirring of the substances while they are being conveyed in order to obtain good transfer of heat, with balanced temperature conditions being achieved very quickly, which is favorable to the treatment insofar as the risk of denaturing the substances is reduced.

Nevertheless, when the mass of substances in divided solid form presents poor fluidity, thus encouraging the formation of slopes, as happens with numerous food or medicinal powders, a technical difficulty is encountered that stirring on its own is not capable of solving. Either the substances cannot be treated because of temperature levels that are too high thereby leading to the substances being denatured, or else the debacterization thereof is insufficient to ensure quasi-total destruction of molds and spores.

BRIEF SUMMARY OF THE INVENTION

An object of the invention is to devise a method and an installation for treating substances in divided solid form for thermal debacterization thereof while avoiding the above-mentioned limitations, and in particular that are well suited to treating powders, in particular food or medicinal powders that present poor fluidity, in order to debacterize them, and to do so without any risk of the substances burning since that would reduce the various organoleptic and/or therapeutic properties thereof.

The above-mentioned technical problem is solved in accordance with the invention by means of a method of treating substances in divided solid form for thermal debacterization, in which the substances are stirred in a closed enclosure provided internally with controlled heating contact wall means acting directly on the substances while they are being stirred, said closed enclosure being connected to a source for supplying wet steam under atmospheric pressure, said steam being superheated prior to penetrating into the enclosure by a heater outside said enclosure, said method being remarkable in that the substances for treatment are previously mixed, prior to reaching an inlet to the closed enclosure, with an anti-clumping agent likewise in the form of divided solids, the mixture then being stirred in the closed enclosure while being subjected to the combined action of the heating contact walls and of the superheated wet steam, and being recovered at an outlet of the closed enclosure.

Thus, because of the presence of the anti-clumping agent, it is possible to ensure that the conveyed mass presents fluidity that is favorable for good heat exchange that goes to the very core of said mass, thus making it possible to maintain a minimum temperature difference throughout the process between the treatment temperature (the temperature of the heating contact walls) and the temperature reached at all points within the substances.

In accordance with a first embodiment, the proportion of anti-clumping agent in the mixture that is admitted into the closed enclosure lies in the range 0.5% to 1% or 2% by weight, so that the mixture recovered at \the outlet from said enclosure is directly usable. In particular, provision may be made for the anti-clumping agent to be in powder form, in particular a powder of inert silicon dioxide, or indeed micronized and debacterized straw or cereal husks.

In accordance with another implementation, the proportion of anti-clumping agent in the mixture admitted into the closed enclosure lies in the range 1% or 2% to 50% by weight, preferably being selected to lie in the range 5% to 15% by weight, and the mixture recovered at the outlet from said enclosure is subjected to mechanical sorting enabling the major fraction of the anti-clumping agent to be removed so that there remains only a residual percentage that does not exceed 1% to 2% by weight.

Under such circumstances, and advantageously, when the method involves treating substances in the form of powders having grain size lying in the range 20 micrometers ($\mu m$) to 300 $\mu m$, it is advantageous for the anti-clumping agent to be in the form of powder or pieces, and for it to be selected to have a grain size that is at least 100 $\mu m$ greater than the grain size of the substances for treatment, so as to enable mechanical sorting to be effective.

In particular, under such circumstances, provision may be made for the anti-clumping agent to be constituted by debacterized straw or cereal husks of large grain size, with a grain size preferably selected to be not less than 500 $\mu m$.

When the anti-clumping agent is constituted by straw or cereal husks, it is possible for example to make use of rice hull or of wheat chaff.

Preferably, and more generally, the treatment is performed continuously, the mixture of substances being stirred and conveyed within the closed enclosure from the upstream inlet to the downstream outlet of said enclosure, while being subjected all along its transit to the combined action of the heating contact walls and of the superheated wet steam.

The invention also provides an installation for implementing a continuous thermal treatment method presenting at least one of the above-mentioned characteristics, said installation being remarkable in that it comprises:

a metering mixer having two feed hoppers respectively dedicated to the substances for treatment 20 and to an anti-clumping agent; and downstream from the metering mixer, a closed enclosure fitted internally with a heating screw having a helical portion comprising a solid piece of material that is electrically conductive and that is connected to a 25 source for supplying it with electrical energy.

Provision may optionally be made for the installation further to comprise, downstream from the closed enclosure, a vibrating screen selected as a function of the respective grain sizes of the substances for treatment and of the anti-clumping agent in order to extract the major fraction of the anti-clumping agent from the mixture treated in the closed enclosure so that there remains only a residual percentage of anti-clumping agent that does not exceed 1% to 2% by weight.

Other characteristics and advantages of the invention appear more clearly in the light of the following description and the accompanying drawing relating to a particular embodiment.

BRIEF DESCRIPTION OF THE DRAWING

Reference is made to the sole FIGURE of the accompanying drawing, which FIGURE is a diagram of an installation implementing a method of treatment, here continuous treatment, that is applied to substances in the form of divided solids for the purpose of thermal debacterization thereof, in accordance with the invention.

DETAILED DESCRIPTION OF A PREFERRED EMBODIMENT

The sole FIGURE of the accompanying drawings shows an installation for performing treatment, here continuous treatment, the installation being given overall reference 10 and serving to perform thermal debacterization of substances in the form of divided solids.

Naturally, the invention is not limited in any way to performing continuous treatment, and it also covers discontinuous treatments, in which the substances for treatment are stirred within a treatment enclosure without being conveyed from an upstream inlet to a downstream outlet of said enclosure.

The installation 10 comprises a closed enclosure 30 (drawn on a larger scale than the other pieces of-equipment of the installation in order to show its components more clearly) that is constituted by an auger having a semicylindrical bottom closed at both ends by end walls 31. The auger is closed on top by a cover 30.1 fitted with an inlet 32 at an upstream end for delivering the substances for treatment, a downstream outlet 33 being provided at its other end to recover the substances after they have been subjected to heat treatment.

Inside the closed space of the enclosure 30 there are disposed controlled means having heating contact walls, specifically constituted by a heater transfer screw 34 having a helical portion 35 that is in the form of a flat helical strip, and that is fastened to a central shaft 36 of axis X. Beyond leaktight bearings 37, the central shaft 36 is extended at each end by respective shaft ends 38, which ends are connected to respective rotary drive means and also electrical power supply means (not shown). The helical portion 35 in this embodiment is made as a solid piece of material that is electrically conductive in order to enable said helical portion to be heated by the Joule effect. Thus, the heating contact walls constituted by the helical portion 35 act directly on the substances while they are being conveyed.

The closed enclosure 30 is also connected to a source 50 for supplying wet steam at atmospheric pressure, said steam coming from a tank 51 being superheated by an electrical resistance heater 52 prior to penetrating via a pipe 53 into the closed enclosure 30, which pipe is fitted with steam injector nozzles 54 arranged inside said enclosure.

There can also be seen a venting circuit 39, shown diagrammatically in the FIGURE, for extracting excess steam.

For greater details concerning the above-described components associated with the closed enclosure 30 and supplying it with superheated wet steam at atmospheric pressure, reference may be made to document WO-A-2009/133321 in the name of the Applicant.

The above means enable the mass that is being conveyed through the closed enclosure to be subjected to uniform heat treatment, with a temperature at the surface of the turns of the heater screw that is substantially identical to the temperature of the steam (generally lying in the range 100° C. to 250° C.) and with a transit time that is adjusted as a function of the substances concerned (generally lying in the range a few seconds to a few minutes).

In accordance with the invention, the substances P for treatment are initially mixed, prior to reaching the upstream inlet 32 of the closed enclosure 30, with an anti-clumping agent p that is likewise in the form of a divided solid, with the mixture then being stirred, and in this embodiment also being conveyed within the closed enclosure 30, while being subjected to the combined action of the heating contact walls 35 and of the superheated wet steam, until it reaches the downstream outlet 33 from the closed enclosure 30.

In the FIGURE, and still in the context of performing continuous treatment, the installation 10 has a metering mixer 20 with two feed hoppers 22, 23 respectively dedicated to feeding the substances P for treatment and the anti-clumping agent p. These two hoppers 22 and 23 are secured to the structure 21 of the metering mixer, and they communicate with a main pipe 24 having a conveyor screw 25 arranged therein and driven in rotation by an associated motor 26. As shown diagrammatically in the FIGURE, provision may optionally be made for the conveyor screw 25 to have single blades for conveying the substances P for treatment and double blades beyond the point where the anti-clumping agent p is injected, in order to improve mixing.

Naturally, in a variant, prior mixing could be performed in a concrete mixer, or by using any other known mixer (e.g. planetary or blade mixer or a ribbon blender), with the mixture for treatment then being injected into a single feed hopper. Nevertheless, mixing in a metering mixer as shown remains more advantageous with operation that is continuous.

The mixture as prepared in this way leaves the metering mixer via its outlet 27 so as to penetrate into the inlet 32 of the closed enclosure 30. It should be observed that there is no point in providing a leaktight airlock at the inlet or the outlet of the closed enclosure 30, since the treatment being performed with wet steam takes place at atmospheric pressure.

The mixture referenced M penetrating into the closed enclosure 30 and transferred by the transfer screw 34 is then subjected to the combined action of the heating contact walls, specifically constituted by the helical portion 35 of the screw 34, and of the superheated wet steam escaping from the injection nozzles 54, until the mixture reaches the downstream outlet 33 of the closed enclosure 30.

Because of the presence of the anti-clumping agent p that has been intimately mixed with the substances P for treatment, the mass of mixture remains fluid, thereby enabling good heat exchange to take place to the very core of the substances, even when using divided solids in the form of powders that easily tend to cake and to form slopes.

Between two adjacent turns of the helical portion 35 of the transfer screw 34, the mass of substances presents thermal gradients that become much smaller as a result of the quality of the heat exchange at all locations within the substances, thereby avoiding excessively high temperatures being reached in the immediate vicinity of the turns, which would lead to a risk of burning, while still having, halfway between two turns, the desired temperature level to ensure good debacterization without any risk of denaturing the substances. This makes it possible to minimize temperature differences between the treatment temperature, which is specifically the temperature of the heating contact turns, and the temperature reached at all points within the substances.

For certain substances in the form of divided solids, it is possible to use an anti-clumping agent at a proportion in the mixture that lies in the range 0.5% to 1% or 2% by weight. Under such circumstances, the mixture recovered at the outlet from the closed enclosure 30 is directly usable as such. The residual percentage of anti-clumping agent must nevertheless comply with the regulations in the countries concerned, which in general are of the order of about 1% in France and 2% in the United States, for example. Thus, for this category of substances, the treatment may be performed with recovery downstream from the closed enclosure 30 being direct and without requiring any subsequent separation treatment, providing the proportion of anti-clumping agent remains very low and in any event compatible with the applicable regulations.

By way of example, for the anti-clumping agent p it is possible to use an agent in the form of a powder, in particular an inert silicon dioxide powder, such as that sold by the supplier Degussa under the trademark Aerosil®, or indeed micronized and debacterized straw or cereal husks. By way of example, for said husks it is possible to use rice hull or wheat chaff. The grain size of such a powder then generally lies in the range a few micrometers to a few tens of micrometers.

For other substances that are more difficult to treat, such as certain food or medical powders (in particular cactus powder, dandelion powder, pigments such as paprika, alfalfa, garlic, or onion powders, or certain particular powders such as *Harpagophytum procumbens*), the above-mentioned proportion of anti-clumping agent may be found to be insufficient, so that it then becomes necessary to use proportions lying rather in the range 1% or 2% to 50% by weight, and preferably lying in the range 5% to 15% by weight. Under such circumstances, it is not possible in general to use the mixture recovered at the outlet from the closed enclosure 30 as such, and it becomes necessary to associate the above-mentioned process by subjecting the mixture recovered at the outlet to mechanical sorting so as to remove the major fraction of the anti-clumping agent so that there remains no more than a residual percentage that does not exceed 1% to 2% by weight.

Thus, in the FIGURE, there can be seen downstream from the closed enclosure 30, a mechanical sorter member such as a vibrating screen 40 that is selected as a function of the grain size of the substances P for treatment and of the grain size of the anti-clumping agent p, so as to extract the major fraction of the anti-clumping agent from the mixture treated in the closed enclosure 30.

For the vibrating screen 40, it is possible to use a vibrating screen having two superposed grids, such as those made in conventional manner by the supplier Sweco. In outline, such a vibrating screen comprises a structure 41 fitted with two superposed grids 42 and 43, the lower grid 43 having a smaller mesh size than the upper grid 42, an outlet 44 for the coarser substances (arrow 46), and a lower outlet 47 in the bottom 46 for the finer substances (arrow 48).

Specifically, the arrow 46 corresponds to recovering the major fraction of the anti-clumping agent p so that only a residual percentage that does not exceed 1% to 2% by weight remains in the main outlet corresponding to the arrow 48. The final recovered substances are then once more entirely compatible with regulatory requirements concerning use.

Preferably, when the substances P for treatment are in the form of a powder of grain size lying in the range 20 µm to 300 µm, provision is made for the anti-clumping agent p to be in the form of a powder or pieces, using a grain size that is at least 100 µm greater than the grain size of the substances P for treatment, so as to ensure that mechanical sorting is effective. This difference in grain size suffices to guarantee good separation in the vibrating screen 40 as a result of the difference in the mesh sizes of the superposed grids 42 and 43. As an indication, a difference of 100 µm corresponds to a difference of about 15 mesh for the superposed screening grids. For example, it is thus possible to use an upper grid 42 of 35 to 40 mesh (500 µm to 420 µm) and a lower grid 43 of about 60 mesh (250 µm).

In particular, for the anti-clumping agent p, it is possible to use an agent constituted by shredded or diced straw or cereal husks (e.g. rice hull or wheat chaff) that has been debacterized and that is of large grain size, e.g. having a grain size that is preferably selected to be not less than 500 µm. This enables good separation of the substances to be achieved downstream from the closed enclosure, for all powders for treatment presenting a grain size lying in the range 100 µm to 300 µm.

This thus enables a treatment method and installation to be provided, here for operating continuously, that achieves excellent thermal debacterization of substances in the form of divided solids, in particular in the form of powders, which is more particularly satisfactory insofar as the appropriate temperature is reached quickly and thus without any risk of denaturing the substances, and with optimized heat exchange within the mass of substances being conveyed due to the presence of the anti-clumping agent procuring the desired degree of fluidity for the medium being treated.

The invention is not limited to the embodiment described above, but on the contrary covers any variant making use of equivalent means to reproduce the essential characteristics set out above. In particular, the invention also covers thermal debacterization treatments that are performed discontinuously, with stirring only (no conveying) within the treatment enclosure.

While the present invention has been illustrated and described with respect to a particular embodiment thereof, it should be appreciated by those of ordinary skill in the art that various modifications to this invention may be made without departing from the spirit and scope of the present invention.

What is claimed is:

1. A method of treating substances in divided solid form for thermal debacterization, in which the substances are stirred in a closed enclosure provided internally with controlled heating contact wall means acting directly on the substances while they are being stirred, said closed enclosure being connected to a source for supplying wet steam under atmospheric pressure, said steam being superheated prior to penetrating into the enclosure by a heater outside said enclosure, wherein the substances for treatment are previously mixed, prior to reaching an inlet to the closed enclosure, with an anti-clumping agent likewise in the form of divided solids, the mixture then being stirred in the closed enclosure while being subjected to the combined action of the heating contact walls and of the superheated wet steam, and being recovered at an outlet of the closed enclosure.

2. The method according to claim 1, wherein the proportion of anti-clumping agent in the mixture that is admitted into the closed enclosure lies in the range 0.5% to 2% by weight, so that the mixture recovered at the outlet from said enclosure is directly usable.

3. The method according to claim 2, wherein the anti-clumping agent is in powder form, in particular a powder of inert silicon dioxide, or micronized and debacterized straw or cereal husks.

4. The method according to claim 1, wherein the proportion of anti-clumping agent in the mixture admitted into the closed enclosure lies in the range 1% to 50% by weight, preferably being selected to lie in the range 5% to 15% by weight, and the mixture recovered at the outlet from said enclosure is subjected to mechanical sorting enabling the major fraction of the anti-clumping agent to be removed so that there remains only a residual percentage that does not exceed 1% to 2% by weight.

5. The method according to claim 4, wherein the substances for treatment are powders of grain size lying in the range 20 µm to 300 µm, wherein the anti-clumping agent is in the form of powder or pieces, and is selected to have a grain size that is at least 100 µm greater than the grain size of the substances for treatment, so as to enable mechanical sorting to be effective.

6. The method according to claim 4, wherein the anti-clumping agent is constituted by debacterized straw or cereal husks of large grain size, with a grain size preferably selected to be not less than 500 µm.

7. The method according to claim 3, wherein the anti-clumping agent is constituted by rice hull or wheat chaff.

8. The method according to claim 1, wherein the treatment is performed continuously, the mixture of substances being stirred and conveyed within the closed enclosure from the upstream inlet to the downstream outlet of said enclosure, while being subjected all along its transit to the combined action of the heating contact walls and of the superheated wet steam.

9. A method of treating substances in divided solid form for thermal debacterization, in which the substances are stirred in a closed enclosure provided internally with controlled heating contact wall means acting directly on the substances while they are being stirred, said closed enclosure being connected to a source for supplying wet steam under atmospheric pressure, said steam being superheated prior to penetrating into the enclosure by a heater outside said enclosure, wherein the substances for treatment are previously mixed, prior to reaching an inlet to the closed enclosure, with an anti-clumping agent likewise in the form of divided solids, the mixture then being stirred in the closed enclosure while being subjected to the combined action of the heating contact walls and of the superheated wet steam, and being recovered at an outlet of the closed enclosure, wherein the anti-clumping agent is constituted by straw or cereal husks.

\* \* \* \* \*